(12) United States Patent
Zhang et al.

(10) Patent No.: US 11,182,878 B2
(45) Date of Patent: Nov. 23, 2021

(54) SYSTEMS AND METHODS FOR IMPROVING MAGNETIC RESONANCE IMAGING USING DEEP LEARNING

(71) Applicant: Subtle Medical, Inc., Menlo Park, CA (US)

(72) Inventors: Tao Zhang, Mountain View, CA (US); Enhao Gong, Sunnyvale, CA (US)

(73) Assignee: SUBTLE MEDICAL, INC., Menlo Park, CA (US)

( * ) Notice: Subject to any disclaimer, the term of this patent is extended or adjusted under 35 U.S.C. 154(b) by 0 days.

(21) Appl. No.: 17/069,036

(22) Filed: Oct. 13, 2020

(65) Prior Publication Data

US 2021/0042883 A1    Feb. 11, 2021

Related U.S. Application Data

(63) Continuation of application No. PCT/US2019/027826, filed on Apr. 17, 2019.

(60) Provisional application No. 62/659,837, filed on Apr. 19, 2018.

(51) Int. Cl.
*G06K 9/00* (2006.01)
*G01V 3/00* (2006.01)
(Continued)

(52) U.S. Cl.
CPC .............. *G06T 5/002* (2013.01); *A61B 5/055* (2013.01); *A61B 5/7267* (2013.01); *G01R 33/561* (2013.01); *G01R 33/565* (2013.01); *G01R 33/5608* (2013.01); *G01R 33/56545* (2013.01); *G06T 5/001* (2013.01); *G06T 2200/24* (2013.01); *G06T 2207/10088* (2013.01);*G06T 2207/20004* (2013.01); *G06T 2207/20081* (2013.01); *G06T 2207/20084* (2013.01); *G06T 2207/30168* (2013.01)

(58) Field of Classification Search
USPC ........ 382/100, 103, 128–132, 156–157, 168, 382/181, 199, 219, 254, 260, 274, 276, 382/286; 600/449, 160, 103; 601/4; 606/2.5; 324/309, 331
See application file for complete search history.

(56) References Cited

U.S. PATENT DOCUMENTS 8,535,250 B2 * 9/2013 Owen .................. A61B 8/0833
601/4
8,638,096 B2    1/2014 Zhang et al.
(Continued)

FOREIGN PATENT DOCUMENTS

WO    WO-2014036473 A1    3/2014
WO    WO-2019204406       10/2019

OTHER PUBLICATIONS

PCT/US2019/027826 International Search Report and Written Opinion dated Jul. 2, 2019.

*Primary Examiner* — Seyed H Azarian
(74) *Attorney, Agent, or Firm* — Wilson Sonsini Goodrich & Rosati

(57) ABSTRACT

A computer-implemented method is provided for improving image quality with shortened acquisition time. The method comprises: determining an accelerated image acquisition scheme for imaging a subject using a medical imaging apparatus; acquiring a medical image of the subject according to the accelerated image acquisition scheme using the medical imaging apparatus; applying a deep network model to the medical image to improve the quality of the medical image; and outputting an improved quality image of the subject, for analysis by a physician.

14 Claims, 5 Drawing Sheets

(51) Int. Cl.
    *G06T 5/00*     (2006.01)
    *G01R 33/56*     (2006.01)
    *G01R 33/561*     (2006.01)
    *G01R 33/565*     (2006.01)
    *A61B 5/055*     (2006.01)
    *A61B 5/00*     (2006.01)

(56) References Cited

U.S. PATENT DOCUMENTS

| | | |
|---|---|---|
| 10,074,038 B2 | 9/2018 | Hsieh et al. |
| 10,970,887 B2 | 4/2021 | Wang et al. |
| 2009/0299187 A1* | 12/2009 | Bailey ................ A61B 17/2256 |
| | | 600/449 |
| 2012/0081114 A1 | 4/2012 | Weller et al. |
| 2012/0112751 A1 | 5/2012 | Littmann et al. |
| 2012/0316396 A1* | 12/2012 | Robertson ........ A61B 17/22012 |
| | | 600/160 |
| 2013/0293229 A1 | 11/2013 | Lin |
| 2015/0137811 A1 | 5/2015 | Muftuler et al. |
| 2015/0289937 A1* | 10/2015 | Chia .................... A61B 5/0084 |
| | | 606/2.5 |
| 2016/0051125 A1* | 2/2016 | Wolf ................ A61B 17/22004 |
| | | 600/103 |
| 2017/0035319 A1 | 2/2017 | Zhao et al. |
| 2017/0372193 A1 | 12/2017 | Mailhe et al. |
| 2019/0347772 A1 | 11/2019 | Zhang et al. |
| 2020/0151922 A1* | 5/2020 | Xu ......................... A61B 6/563 |
| 2021/0056734 A1* | 2/2021 | Han .................. G01R 33/5608 |

\* cited by examiner

SYSTEMS AND METHODS FOR IMPROVING MAGNETIC RESONANCE IMAGING USING DEEP LEARNING

CROSS-REFERENCE TO RELATED APPLICATION

This application is a Continuation Application of International Patent Application No. PCT/US2019/027826, filed on Apr. 17, 2019, which claims priority to U.S. Provisional Application No. 62/659,837 filed on Apr. 19, 2018, each of which is incorporated herein by reference in its entirety.

BACKGROUND

Magnetic Resonance Imaging (MRI), or nuclear magnetic resonance imaging, is a medical imaging technique commonly used to visualize a subject (e.g., patient) particularly the detailed internal structures in the body. MRI provides clinical image with improved resolution, high contrast between the different soft tissues of the body, without involving ionizing radiation, and is therefore an ideal imaging modality for many challenging diseases. Compared with other modalities such as X-ray, CT and ultrasound, MRI takes longer time, sometimes several minutes, for data acquisition to generate clinically useful images. Undesirable imaging artifacts may appear due to the long scan time. Such long scan time for MR exams may result in high imaging cost and limit the patient volume and accessibility. Some MR applications (e.g., diffusion-weighted imaging) require the repetition of the same or similar acquisition for multiple times in order to achieve adequate signal-to-noise ratio (SNR).

Methods such as parallel imaging and compressed sensing, have been employed for accelerated MR image acquisition, however the practical acceleration capability is still limited. For example, when the scan time is significantly shortened, parallel imaging suffers from aliasing artifact along with dramatically amplified noise. In another example, compressed sensing suffers from image blurring. Conventional methods may achieve accelerated data acquisition by: (1) reducing number of repetitions, (2) undersampling beyond the Nyquist sampling rate, or (3) reducing image resolution. Such methods may result in images with various artifacts such as low SNR, aliasing or blurring.

The term "repetition," as used herein, generally refers to repetition of image acquisitions using the same imaging parameters on the same subject, repetition of image acquisitions using varied imaging parameters on the same subject, repetition of image acquisitions on a subject from varied angles or the like, thereby achieving enhanced image quality. For instance, in Arterial Spin Labeling (ASL) MRI, there can be multi-delay ASL that the high quality images may be computed using certain model based or weighted average of multiple images acquired using the same imaging parameters but not the same delay parameters. In another example, a COSMOS method may be used for achieving high quality image in Quantitative Susceptibility Mapping (QSM) MRI, The method is model-based or weighted average of multiple images acquired using the same imaging parameters. During the repeated image acquisition, the subject may be imaged from different angles (e.g., rotate or move their head to various positions) using the same imaging parameters.

One of the conventional methods is Multi-NEX (number of excitations) acquisition, which is referred to the method of repeating the same or similar acquisition multiple times to improve SNR for MRI. Define m as the ground truth image, $m_i$ as the acquired image for the i-th acquisition, and $n_i$ as the corresponding noise or offsets from the ground-truth in $m_i$. Then, $$m_i = m + n_i,$$

Typically, the average, including linear averaging or weighted averaging that possibly based on certain weighting models, of all acquired images $m_{ave}$ has higher SNR than any individual image $m_i$, and it is considered to be an estimate of m. Alternatively, an image denoising method can be used to improve the SNR of $m_i$. This process can be represented by, $$\hat{m} = f(m_i),$$

where $f$ represents a denoising function, and the denoised image $\hat{m}$ is the estimate of m. However, this approach has not been as widely used in the past as simple averaging for most multi-NEX acquisitions.

Parallel imaging and compressed sensing are two popular conventional methods for accelerating MR acquisitions by sampling beyond the Nyquist sampling rate. Parallel imaging uses a set of coil arrays with different coil sensitivity to synthesize un-acquired data, while compressed sensing utilizes a sparsity constraint and obtains an estimate of the underlying image by solving an optimization problem. Commonly, parallel imaging and compressed sensing are combined to achieve better image quality and acceleration capability. Define $m_u$ as the image from the undersampled acquisition, then both parallel imaging and compressed sensing can be formulated as:

$$\hat{m} = f(m_u),$$

where $f$ represents the corresponding image reconstruction, and $\hat{m}$ is the estimated reconstruction. However, such methods may achieve better image quality at the expense of hardware infrastructures or acquisition time.

Super resolution is another conventional method for image resolution improvement: the original image $m_{LR}$ is acquired with low resolution, and the reconstructed image $m_{SR}$ is with better image resolution. $m_{SR}$ can be obtained by increasing the matrix size of $m_{LR}$ and estimating the additional high spatial frequency contents that have not been acquired. Since low resolution images require less acquisition time, the super resolution method can also shorten MR scan time.

Similar to the previous formulations, the super resolution reconstruction can also be represented by a function $f$ that transforms a low resolution image to a high resolution image $\hat{m}$.

$$\hat{m} = f(m_{LR}),$$

The major challenge for the super resolution method is that the un-acquired high spatial frequency information (or function $f$) is difficult to estimate directly. Thus, a need exists for an improved system for MR imaging.

SUMMARY

The present disclosure provides improved Magnetic Resonance Imaging (MRI) systems that can address various drawbacks of conventional systems, including those recognized above. Method and system of the presenting disclosure provide improved image quality with shortened image acquisition time. The computation time for image reconstruction in runtime may also be reduced compared to the standard iterative reconstruction methods. The provided method and system may significantly reduce MR scan time by applying deep learning techniques for image reconstruction so as to enhance image quality. Examples low quality in medical imaging may include noise (e.g., low signal noise ratio), blur (e.g., motion artifact), shading (e.g., blockage or interference with sensing), missing information (e.g., missing pixels or voxels in painting due to removal of information or masking), reconstruction (e.g., degradation in the measurement domain), and/or under-sampling artifacts (e.g., under-sampling due to compressed sensing, aliasing). Methods and systems of the present disclosure can be applied to existing systems seamlessly without a need of a change of the underlying infrastructure. In particular, the provided methods and systems may improve MR image quality at no additional cost of hardware component and can be deployed regardless of the configuration or specification of the underlying infrastructure.

In an aspect of the invention, a computer-implemented method is provided for improving image quality with shortened acquisition time. The method comprises: determining an accelerated image acquisition scheme for imaging a subject using a medical imaging apparatus; acquiring, using the medical imaging apparatus, a medical image of the subject according to the accelerated image acquisition scheme; applying a deep network model to the medical image to improve the quality of the medical image; and outputting an improved quality image of the subject for analysis by a physician. In some embodiments, the medical image includes a magnetic resonance image.

In some embodiments of the invention, determining the accelerated image acquisition scheme comprises: receiving a target acceleration factor or target acquisition speed via a graphical user interface, and selecting from a plurality of accelerated image acquisition schemes based on the target acceleration factor or the target acquisition speed. In some cases, the accelerated image acquisition scheme is selected by applying the plurality of accelerated image acquisition schemes to a portion of the medical image for simulation.

In some embodiments, the accelerated image acquisition scheme is determined based on user input and real-time simulated output images. In some embodiments, the accelerated image acquisition scheme comprises one or more parameters related to an undersampled k-space, an undersampling pattern, and a reduced number of repetitions. In some cases, the undersampling pattern is selected from a group consisting of a uniform undersampling pattern, a random undersampling pattern, and a variable undersampling pattern. In some embodiments, the medical image comprises undersampled k-space image or image acquired using reduced number of repetitions.

In some embodiments, the deep learning model is trained with adaptively optimized metrics based on user input and real-time simulated output images. In some embodiments, the deep learning model is trained using training datasets comprising at least a low quality image and a high quality image. In some cases, the low quality image is generated by applying one or more filters or adding synthetic noise to the high quality image to create noise or undersampling artifacts. In some embodiments, the deep learning model is trained using image patches that comprise a portion of at least a low quality image and a high quality image. In some cases, the image patches are selected based on one or more metrics quantifying an image similarity.

In some embodiments, the deep learning model is a deep residual learning model. In some embodiments, the deep learning model is trained by adaptively tuning one or more model parameters to approximate a reference image. In some embodiments, the improved quality image of the subject has greater SNR, higher resolution, or less aliasing compared with the medical image acquired using the medical imaging apparatus.

Another aspect of the present disclosure provides a non-transitory computer readable medium comprising machine executable code that, upon execution by one or more computer processors, implements any of the methods above or elsewhere herein. For example, the one or more processors may perform operations that comprise: determining an accelerated image acquisition scheme for imaging a subject using a medical imaging apparatus; acquiring, using the medical imaging apparatus, a medical image of the subject according to the accelerated image acquisition scheme; applying a deep network model to the medical image to improve the quality of the medical image; and outputting an improved quality image of the subject for analysis by a physician.

In some embodiments, the medical image includes a magnetic resonance image. In some embodiments, the accelerated image acquisition scheme is determined based on user input and real-time simulated output images. In some embodiments, the accelerated image acquisition scheme comprises one or more parameters related to an undersampled k-space, an undersampling pattern, and a reduced number of repetitions.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and descriptions are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein) of which:

DETAILED DESCRIPTION

Figure 1:
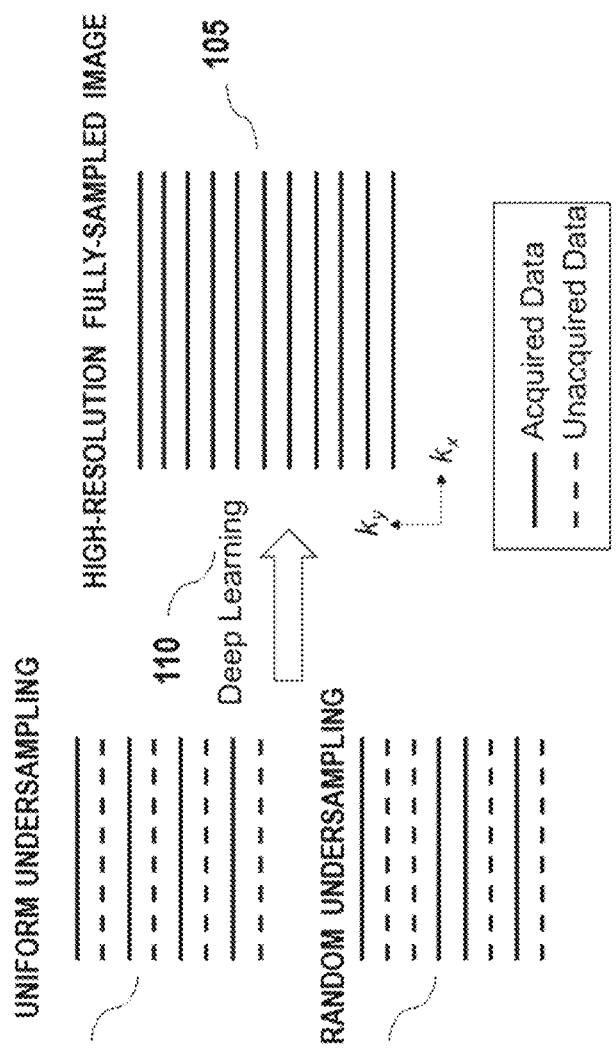
FIG. 1 schematically illustrates an example of transforming low quality image to high quality image using a deep learning algorithm.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Accelerated Acquisition

The term "accelerated acquisition," as used herein, generally refers to shortened MR acquisition time. The provided system and method may be able to achieve MR imaging with improved quality by an acceleration factor of at least 1.5, 2, 3, 4, 5, 10, 15, 20, a factor of a value above 20 or below 1.5, or a value between any two of the aforementioned values. An accelerated acquisition can be achieved via approaches such as: (1) reducing the number of repetitions for multi-NEX acquisition, (2) reducing the sampling rate below the Nyquist rate, or (3) reducing the image resolution. An acceleration scheme may comprise using one or more of the above approaches. An acceleration scheme may comprise using any combination of the above approaches. In an example, the accelerated acquisition may be achieved by reducing the number of repetitions. In another example, the accelerated acquisition may be achieved by undersampling the k-space. In a further example, the accelerated acquisition may be achieved by a combination of reducing the number of repetition and undersampling the k-space. An acceleration scheme may also comprise one or more parameters that may affect an acceleration result of a selected approach. An acceleration scheme may also be referred to as acquisition scheme or accelerated image acquisition scheme which are used interchangeably throughout the specification.

Image formation in MR imaging is based on the traversal of k-space in two or three dimensions in a manner determined by the pulse sequence. Although acquisition of data in the frequency-encoding direction is typically rapid and on the order of several milliseconds, a separate echo collected with a slightly different value of the applied phase-encoding gradient is required to sample each value of $k_y$ along the phase-encoding axis. The sampling of k-space through a prescribed number of phase-encoding steps therefore accounts for the majority of the acquisition time in most MR imaging acquisitions.

In some cases, the accelerated data acquisition may be achieved by undersampling the k-space. The k-space can be undersampled according to various sampling schemes. The sampling scheme may include at least a sampling density along a given direction, or a predefined pattern/trajectory. For example, k-space may be undersampled least along a given direction, by virtue of the density of samples relative to the Nyquist criterion for the intended image's FOV (field of view) of at least 1%, 5%, 10%, 15%, 20%, 25%, 30%, 35%, 40%, 45%, 50% and the like. The sampling scheme may comprise various other factors such as specifying a region of k-space is undersampled, oversampled or critically sampled. In some embodiments, one or more parameters related to a sampling scheme may be specified in an acceleration scheme.

In some embodiments, an undersampling pattern for accelerated acquisition may be specified in an acceleration scheme. The accelerated acquisition may use an undersampling pattern such as uniform undersampling patterns, random undersampling patterns, or variable undersampling patterns. Various patterns or trajectories such as spiral sampling pattern, radially arranged strips, rectilinear pattern, Poisson-disc, jittered grid or randomized pattern may be applied for sampling k-space. The pattern or trajectory may be determined according to a specific imaging technique. For example, to achieve a better parallel reconstruction, the sampling pattern should not contain frequently occurring large gaps. Therefore, Poisson-disc and jittered grid with uniform or variable sampling density may be selected as sampling patterns for parallel processing.

As aforementioned, images acquired under shortened acquisition time may experience various artifacts. Such images may have lower quality such as low SNR, blurring or aliasing. Methods and systems of the present disclosure may mitigate these artifacts by applying a machine learning method to the low quality images resulting in high quality MR image with accelerated acquisition. Such method may be used for image reconstruction and can be used in combination with any existing MR techniques.

Deep Learning Method

FIG. 1 schematically illustrates an example of transforming low quality image 101, 103 to high quality image 105 using deep learning algorithm 110. The low quality image may be acquired using accelerated data acquisition approaches as described above. In some cases, the accelerated data acquisition approach may be specified in an acquisition scheme. Define $m_{acc}$ as the image corresponding to the accelerated data acquisition. An example of accelerated 2D acquisition with reduced sampling rate and/or reduced image resolution is shown in FIG. 1. During the image reconstruction, a deep learning algorithm may be applied to the low quality image to estimate a function $f$ that transforms the low quality image $m_{acc}$ to a high quality image $\tilde{m}$. The high quality image may be high SNR, alias-free, or high resolution image. In some cases, this function $f$ may be obtained by optimizing metrics g between the ground truth image m and the estimated image $\tilde{m}$ through a training process on a number of training datasets:

$$\min \Sigma g_i(k(m), k(\tilde{m})),$$

$$s.t. \tilde{m} = f(m_{acc})$$

There can be one or more cost metrics which can be combined with optimized weightings. g can be any suitable metrics such as $l_2$ norm $\|k(m)-k(\tilde{m})\|^2$, $l_1$ norm $\|k(m)-k(\tilde{m})\|_1$, structural dissimilarity or other metrics. In some cases, k can be identity transform then the metrics are calculated in the image domain. k can be any other transforms, such as Fourier transform, therefore the metrics may be calculated in the corresponding frequency domain. In some cases, the g metric may be used as criteria during the training process of the deep learning model. In some cases, the g metrics can also be a network model that is separately or simultaneously trained together with $f$, to discriminate image states and evaluate image quality. In some cases, the deep learning model may be trained with adaptively optimized metrics based on user input and real-time simulated output images.

The machine learning method 110 may comprise one or more machine learning algorithms. The artificial neural network may employ any type of neural network model, such as a feedforward neural network, radial basis function network, recurrent neural network, convolutional neural network, deep residual learning network and the like. In some embodiments, the machine learning algorithm may comprise a deep learning algorithm such as convolutional neural network (CNN). Examples of machine learning algorithms may include a support vector machine (SVM), a naïve Bayes classification, a random forest, a deep learning model such as neural network, or other supervised learning algorithm or unsupervised learning algorithm. In some cases, the method may be a supervised deep machine learning method.

The deep learning network such as CNN may comprise multiple layers. For example, the CNN model may comprise at least an input layer, a number of hidden layers and an output layer. A CNN model may comprise any total number of layers, and any number of hidden layers. The simplest architecture of a neural network starts with an input layer followed by a sequence of intermediate or hidden layers, and ends with output layer. The hidden or intermediate layers may act as learnable feature extractors, while the output layer in this example provides MR images with improved quality.

Each layer of the neural network may comprise a number of neurons (or nodes). A neuron receives input that comes either directly from the input data (e.g., low quality image data, undersampled k-space data, etc.) or the output of other neurons, and performs a specific operation, e.g., summation. In some cases, a connection from an input to a neuron is associated with a weight (or weighting factor). In some cases, the neuron may sum up the products of all pairs of inputs and their associated weights. In some cases, the weighted sum is offset with a bias. In some cases, the output of a neuron may be gated using a threshold or activation function. The activation function may be linear or non-linear. The activation function may be, for example, a rectified linear unit (ReLU) activation function or other functions such as saturating hyperbolic tangent, identity, binary step, logistic, arcTan, softsign, parameteric rectified linear unit, exponential linear unit, softPlus, bent identity, softExponential, Sinusoid, Sinc, Gaussian, sigmoid functions, or any combination thereof.

In some embodiments, the training process of the deep learning model may employ a residual learning method. In some instances, the residual learning framework may be used for evaluating a trained model. In some instances, the residual learning framework with skip connections may generate estimated ground-truth images from the lower quality images such as complex-valued aliased ones, with refinement to ensure it is consistent with measurement (data consistency). The lower quality input image can be simply obtained via inverse Fourier Transform (FT) of under-sampled data. In some cases, what the model learns is the residual of the difference between the raw image data and ground-truth image data, which is sparser and less complex to approximate using the network structure. The method may use by-pass connections to enable the residual learning. In some cases, a residual network may be used and the direct model output may be the estimated residual/error between low-quality and high quality images. In other word, the function to be learned by the deep learning framework is a residual function which in some situations may be easy to optimize. The higher quality image can be recovered by adding the low quality image to the residual. This residual training approach may reduce the complexity of training and achieve better performance, where the output level is small, reducing the likelihood of introducing large image artifacts even when the model does not predict perfectly.

The training datasets may be input to a deep network comprising residual learning and a convolutional neural network. The model may be trained using a reference image of target quality that has a relatively high SNR and better resolution. In some cases, the deep learning model may be trained with adaptively tuned parameters based on user input and real-time simulated output images. Alternatively or in addition to, the deep learning network may be a "plain" CNN that does not involve residual learning. In some cases, a type of deep learning network may be selected based on the goal of the MR image enhancement, image data characteristics or other factors. For example, according to different goal of image enhancement such as to improve SNR, to achieve alias-free, or to increase resolution image, a deep residual learning network or a plain CNN may be selected. In some cases, during the training process, the deep learning model may adaptively tune model parameters to approximate the reference image of target quality from an initial set of the input images, and outputting an improved quality image.

In some embodiments, the training process of the deep learning model may employ a patch-based approach. In some cases, the image used for training (e.g., low quality and high quality images) may be divided into patches. For example, a pair of training images such as a pair of high quality image and lower quality image may each be divided spatially into a set of smaller patches. The high quality image and the lower quality image can be divided into a set of patches. A size of an image patch may be dependent on the application such as the possible size a recognizable feature contained in the image. Alternatively, the size of an image patch may be pre-determined or based on empirical data.

In some cases, one or more patches may be selected from the set of patches and used for training the model. In some instances, one or more patches corresponding to the same coordinates may be selected from a pair of images. Alternatively, a pair of patches may not correspond to the same coordinates. The selected pair of patches may then be used for training. In some cases, patches from the pair of images with similarity above a pre-determined threshold are selected. One or more pairs of patches may be selected using any suitable metrics quantifying image similarity. For instance, one or more pairs of patches may be selected by calculating a structural similarity index, peak signal-to-noise ratio (PSNR), mean squared error (MSE), absolute error, other metrics or any combination of the above. In some cases, the similarity comparison may be performed using sliding window over the image.

The deep learning model 110 may be trained using one or more training datasets comprising the MR image data. In an example, the training dataset may be 3D volume image data comprising multiple axial slices, and each slice may be complex-valued images each may include two channels for real and imaginary components. The training dataset may comprise lower quality images obtained from MR imaging devices. For example, the low quality input image can be simply obtained via inverse Fourier Transform (FT) of undersampled data (e.g., k-space data). In some cases, the training dataset may comprise augmented datasets obtained from simulation. For instance, image data from clinical database may be used to generate low quality image data. In an example, FFT and filters may be applied to raw image data to transform it to low quality image data such as by applying masks to remove certain data points so as to create artifacts. In another example, image blurring filters may be applied directly on the high quality images to generate low quality images. In a further example, synthetic noise may be added to high quality images to create noisy images. In some embodiments, the higher quality input image data may be obtained from direct image acquisition using an MR imaging device with longer acquisition time or repeated image acquisitions as described elsewhere herein.

The trained deep learning model may be used for transforming input data comprising lower quality MR image data to output data comprising higher quality MR image data. In some cases, the input data may be 3D volume comprising multiple axial slices. In an example, an input and output slices may be complex-valued images of the same size and each include two channels for real and imaginary components. With aid of the provided system, higher quality MR image may be obtained with accelerated acquisition.

In some embodiments, during the training phase additional image processing steps can be applied to the deep learning input images based on users' preference. For example, image filters such as high pass filter, low pass filter and the like can be applied to the input images. In some cases, synthetic noise may be added to the input images. Similarly, post image processing steps can be applied to the deep learning output images based on users' preference. For example, image filters such as high pass filter, low pass filter and the like can be applied to the output images. In some cases, synthetic noise may be added to the output images.

Systems and methods of the present disclosure may provide an imaging accelerator system can be implemented on any existing MR imaging system without a need of a change of hardware infrastructure. The imaging accelerator system may be implemented in software, hardware, firmware, embedded hardware, standalone hardware, application specific-hardware, or any combination of these. The imaging accelerator system can be a standalone system that is separate from the MR imaging system. Alternatively or in addition to, the imaging accelerator system can be integral to the MR imaging system such as a component of a controller of the MR imaging system.

System Overview

Figure 2:
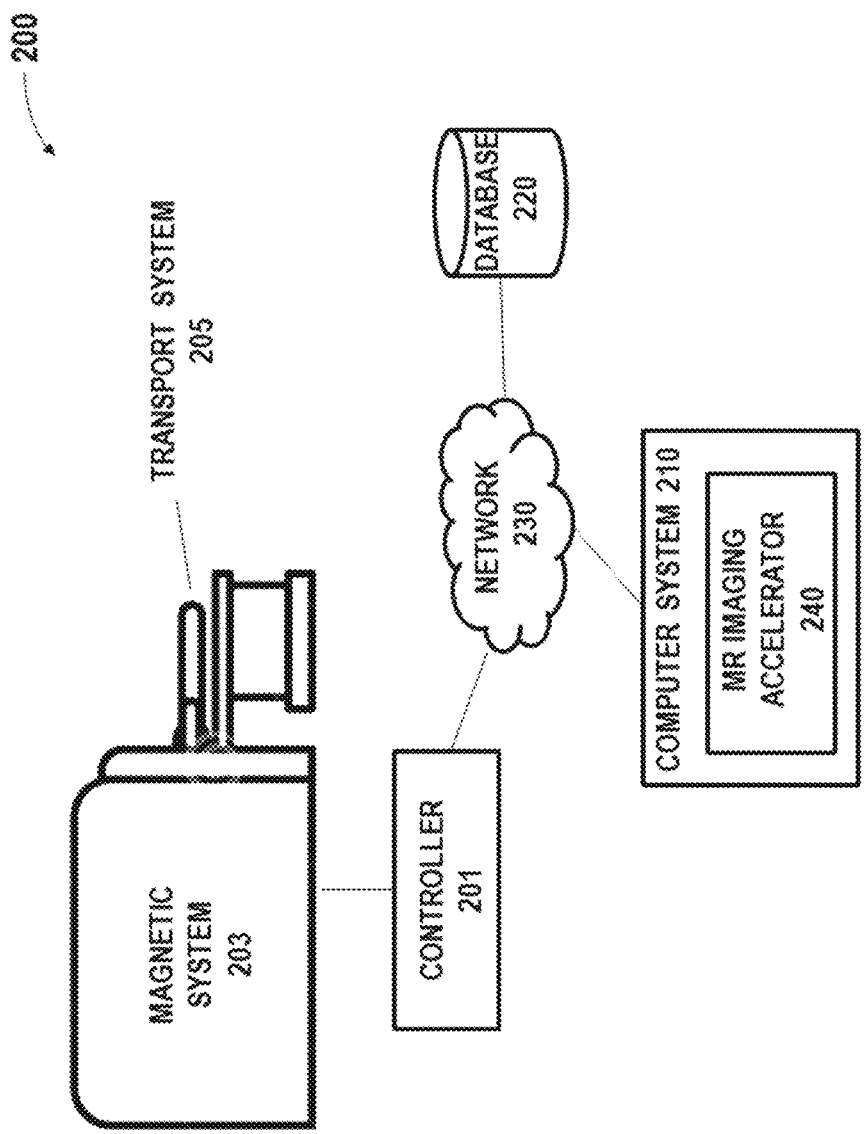
FIG. 2 schematically illustrates a magnetic resonance imaging (MRI) system in which an imaging accelerator of the presenting disclosure may be implemented.

FIG. 2 schematically illustrates a magnetic resonance imaging (MRI) system 200 in which an imaging accelerator 240 of the presenting disclosure may be implemented. The MRI system 200 may comprise a magnet system 203, a patient transport table 205 connected to the magnet system, and a controller 201 operably coupled to the magnet system. In one example, a patient may lie on the patient transport table 205 and the magnet system 203 would pass around the patient. The controller 201 may control magnetic fields and radio frequency (RF) signals provided by the magnet system 203 and may receive signals from detectors in the magnet system 203. The MRI system 200 may further comprise a computer system 210 and one or more databases operably coupled to the controller 201 over the network 230. The computer system 210 may be used for implementing the MR imaging accelerator 240. The computer system 210 may be used for generating an imaging accelerator using training datasets. Although the illustrated diagram shows the controller and computer system as separate components, the controller and computer system can be integrated into a single component.

The controller 201 may be operated to provide the MRI sequence controller information about a pulse sequence and/or to manage the operations of the entire system, according to installed software programs. The controller may also serve as an element for instructing a patient to perform tasks, such as, for example, a breath hold by a voice message produced using an automatic voice synthesis technique. The controller may receive commands from an operator which indicate the scan sequence to be performed. The controller may comprise various components such as a pulse generator module which is configured to operate the system components to carry out the desired scan sequence, producing data that indicate the timing, strength and shape of the RF pulses to be produced, and the timing of and length of the data acquisition window. Pulse generator module may be coupled to a set of gradient amplifiers to control the timing and shape of the gradient pulses to be produced during the scan. Pulse generator module also receives patient data from a physiological acquisition controller that receives signals from sensors attached to the patient, such as ECG (electrocardiogram) signals from electrodes or respiratory signals from a bellows. Pulse generator module may be coupled to a scan room interface circuit which receives signals from various sensors associated with the condition of the patient and the magnet system. A patient positioning system may receive commands through the scan room interface circuit to move the patient to the desired position for the scan.

The controller 201 may comprise a transceiver module which is configured to produce pulses which are amplified by an RF amplifier and coupled to RF coil by a transmit/receive switch. The resulting signals radiated by the excited nuclei in the patient may be sensed by the same RF coil and coupled through transmit/receive switch to a preamplifier. The amplified nuclear magnetic resonance (NMR) signals are demodulated, filtered, and digitized in the receiver section of transceiver. Transmit/receive switch is controlled by a signal from pulse generator module to electrically couple RF amplifier to coil for the transmit mode and to preamplifier for the receive mode. Transmit/receive switch may also enable a separate RF coil (for example, a head coil or surface coil, not shown) to be used in either the transmit mode or receive mode.

The NMR signals picked up by RF coil may be digitized by the transceiver module and transferred to a memory module coupled to the controller. The receiver in the transceiver module may preserve the phase of the acquired NMR signals in addition to signal magnitude. The down converted NMR signal is applied to an analog-to-digital (A/D) converter (not shown) which samples and digitizes the analog NMR signal. The samples may be applied to a digital detector and signal processor which produces in-phase (I) values and quadrature (Q) values corresponding to the received NMR signal. The resulting stream of digitized I and Q values of the received NMR signal may then be employed to reconstruct an image. The provided imaging accelerator may be used for reconstructing the image to achieve an improved quality.

The controller 201 may comprise or be coupled to an operator console (not shown) which can include input devices (e.g., keyboard) and control panel and a display. For example, the controller may have input/output (I/O) ports connected to an I/O device such as a display, keyboard and printer. In some cases, the operator console may communicate through the network with the computer system 210 that enables an operator to control the production and display of images on a screen of display. The images may be MR images with improved quality acquired according to an accelerated acquisition scheme. The image acquisition scheme may be determined automatically by the imaging accelerator 240 and/or by a user as described later herein.

The MRI system 200 may comprise a user interface. The user interface may be configured to receive user input and output information to a user. The user input may be related to control of image acquisition. The user input may be related to the operation of the MRI system (e.g., certain threshold settings for controlling program execution, parameters for controlling the joint estimation of coil sensitivity and image reconstruction, etc). The user input may be related to various operations or settings about the imaging accelerator. The user input may include, for example, a selection of a target location, displaying settings of a reconstructed image, customizable display preferences, selection of an acquisition scheme, settings of a selected acquisition scheme, and various others. The user interface may include a screen such as a touch screen and any other user interactive external device such as handheld controller, mouse, joystick, keyboard, trackball, touchpad, button, verbal commands, gesture-recognition, attitude sensor, thermal sensor, touch-capacitive sensors, foot switch, or any other device.

The MRI platform 200 may comprise computer systems 210 and database systems 220, which may interact with the controller. The computer system can comprise a laptop computer, a desktop computer, a central server, distributed computing system, etc. The processor may be a hardware processor such as a central processing unit (CPU), a graphic processing unit (GPU), a general-purpose processing unit, which can be a single core or multi core processor, a plurality of processors for parallel processing, in the form of fine-grained spatial architectures such as a field programmable gate array (FPGA), an application-specific integrated circuit (ASIC), and/or one or more Advanced RISC Machine (ARM) processors. The processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations. Details regarding the computer system are described with respect to FIG. 3.

The MRI system 200 may comprise one or more databases. The one or more databases 220 may utilize any suitable database techniques. For instance, structured query language (SQL) or "NoSQL" database may be utilized for storing MR image data, raw image data, reconstructed image data, training datasets, trained model, parameters of an acquisition scheme, etc. Some of the databases may be implemented using various standard data-structures, such as an array, hash, (linked) list, struct, structured text file (e.g., XML), table, JSON, NOSQL and/or the like. Such data-structures may be stored in memory and/or in (structured) files. In another alternative, an object-oriented database may be used. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the database of the present disclosure is implemented as a data-structure, the use of the database of the present disclosure may be integrated into another component such as the component of the present invention. Also, the database may be implemented as a mix of data structures, objects, and relational structures. Databases may be consolidated and/or distributed in variations through standard data processing techniques. Portions of databases, e.g., tables, may be exported and/or imported and thus decentralized and/or integrated.

The network 230 may establish connections among the components in the MRI platform and a connection of the MRI system to external systems. The network 230 may comprise any combination of local area and/or wide area networks using both wireless and/or wired communication systems. For example, the network 230 may include the Internet, as well as mobile telephone networks. In one embodiment, the network 230 uses standard communications technologies and/or protocols. Hence, the network 230 may include links using technologies such as Ethernet, 802.11, worldwide interoperability for microwave access (WiMAX), 2G/3G/4G mobile communications protocols, asynchronous transfer mode (ATM), InfiniBand, PCI Express Advanced Switching, etc. Other networking protocols used on the network 230 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), and the like. The data exchanged over the network can be represented using technologies and/or formats including image data in binary form (e.g., Portable Networks Graphics (PNG)), the hypertext markup language (HTML), the extensible markup language (XML), etc. In addition, all or some of links can be encrypted using conventional encryption technologies such as secure sockets layers (SSL), transport layer security (TLS), Internet Protocol security (IPsec), etc. In another embodiment, the entities on the network can use custom and/or dedicated data communications technologies instead of, or in addition to, the ones described above.

Acquisition Scheme

In some embodiments, the MR imaging accelerator of the presenting disclosure may enable accelerated image acquisition with improved image quality. In some cases, an acquisition scheme may be automatically selected and/or determined by the imaging accelerator. In some cases, an acquisition scheme may be selected or defined by a user. One or more parameters of an acquisition scheme may include, for example, the number of encoding steps, the k-space sampling pattern, image resolution, field-of-view, scanning speed, sampling schemes such as pattern, fully sampled regions, undersampled, regions, and various others. In some cases, the acquisition scheme may also include selecting a reconstruction method or setting one or more parameters related to a reconstruction method.

Imaging Accelerator System

Figure 3:
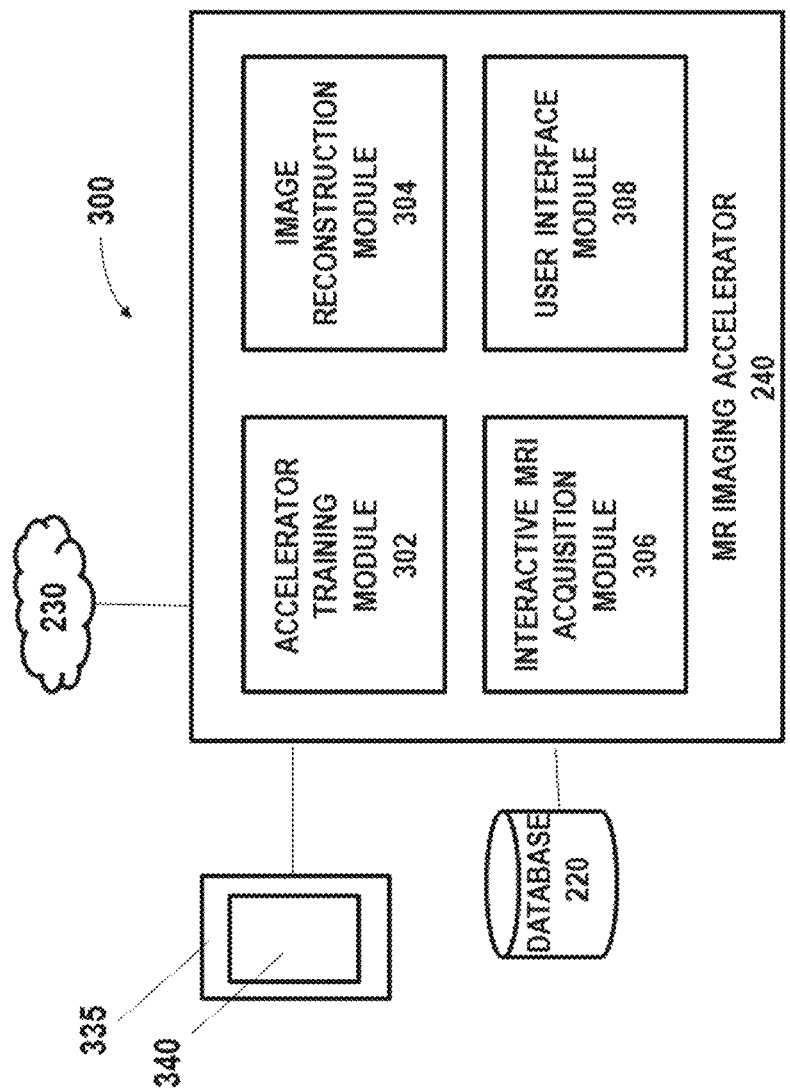
FIG. 3 shows a block diagram of an example of a MR imaging accelerator system, in accordance with embodiments of the present disclosure.

FIG. 3 shows a block diagram of an example of a MR imaging accelerator system 300, in accordance with embodiments of the present disclosure. The MR imaging accelerator system 300 may comprise an MR imaging accelerator 240 which can be the same as the imaging accelerator as described in FIG. 2. The MR imaging accelerator 240 may comprise multiple components, including but not limited to, an accelerator training module 302, an image reconstruction module 304, an interactive MRI acquisition module 306 and a user interface module 308.

The accelerator training module 302 may be configured to obtain and manage training datasets. The accelerator training module 302 may comprise a deep learning algorithm such as convolutional neural network (CNN). The accelerator training module may be configured to implement the machine learning methods as described above. The accelerator training module may train a model off-line. Alternatively or additionally, the accelerator training module may use real-time data as feedback to refine the model.

The image reconstruction module 304 may be configured to reconstruct images using a trained model obtained from the accelerator training module. The image reconstruction module may take one or more k-space images or lower quality MR image data as input and output MR image data with improved quality.

The interactive MRI acquisition module 306 may be operably coupled to the image reconstruction module and/or the controller of the MRI system. The interactive MRI acquisition module 306 may be configured to generate an acquisition scheme. In some cases, the interactive MRI acquisition module may receive a user input indicating a desired acceleration (e.g., acceleration factor, acquisition speed, image resolution, field of view, target region, etc). In response to receiving the target or desired acceleration, the interactive MRI acquisition module may run tests on one or more acquisition schemes and determine an optimal acquisition scheme. The optimal acquisition scheme may be determined based on a predetermined rule. For instance, the optimal acquisition scheme may be determined based on the quality of the output image. For example, an acquisition scheme meeting the target acceleration goal while providing the best quality images may be selected. In some case, the interactive MRI acquisition module may allow a user to define an acquisition scheme. In response to receiving a user defined acquisition scheme, the interactive MRI acquisition module may run simulations and generate output images associated with the acquisition scheme. A user may or may not further adjust the acquisition scheme so as to change the quality or other characteristics of the output images. The determined acquisition scheme may then be transmitted to the controller of the MRI system for controlling the operation of the imaging system as described elsewhere herein. The interactive MRI acquisition module may be operably coupled to the user interface module 308 for receiving user input and outputting an auto-generated acquisition scheme or simulated images.

The user interface module 308 may render a graphical user interface (GUI) 340 allowing a user to select an acquisition scheme, modify one or more parameters of an acquisition scheme, viewing information related to imaging and acquisition settings and the like. The GUI may show graphical elements that permit a user to view or access information related to image acquisition. A graphical user interface can have various interactive elements such as buttons, text boxes and the like, which may allow a user to provide input commands or contents by directly typing, clicking or dragging such interactive elements. For example, a user may manually create or modify a scanning pattern, select an acceleration factor and set other parameters via the GUI. Further details are described later herein with respect to FIG. 4.

In some cases, the graphical user interface (GUI) or user interface may be provided on a display 335. The display may or may not be a touchscreen. The display may be a light-emitting diode (LED) screen, organic light-emitting diode (OLED) screen, liquid crystal display (LCD) screen, plasma screen, or any other type of screen. The display may be configured to show a user interface (UI) or a graphical user interface (GUI) rendered through an application (e.g., via an application programming interface (API) executed on the local computer system or on the cloud).

The imaging accelerator system 300 may be implemented in software, hardware, firmware, embedded hardware, standalone hardware, application specific-hardware, or any combination of these. The imaging accelerator system, modules, components, algorithms and techniques may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device. These computer programs (also known as programs, software, software applications, or code) may include machine instructions for a programmable processor, and may be implemented in a high-level procedural and/or object-oriented programming language, and/or in assembly/machine language. As used herein, the terms "machine-readable medium" and "computer-readable medium" refer to any computer program product, apparatus, and/or device (such as magnetic discs, optical disks, memory, or Programmable Logic Devices (PLDs)) used to provide machine instructions and/or data to a programmable processor. The imaging accelerator system can be a standalone system that is separate from the MR imaging system. Alternatively or in addition to, the imaging accelerator system can be integral to the MR imaging system such as a component of a controller of the MR imaging system.

In some cases, the imaging accelerator system may employ an edge intelligence paradigm that data processing and MR image enhancement is performed at the edge or edge gateway (MRI system). In some instances, machine learning model may be built, developed and trained on a cloud/data center and run on the MRI system (e.g., hardware accelerator). For example, software that run on the edge may be the image reconstruction module 304. Software that run on the cloud or an on-premises environment may be the accelerator training module for training, developing, and managing the deep learning models or the interactive MRI acquisition module 306 to remotely configure the MRI controller.

Figure 4:
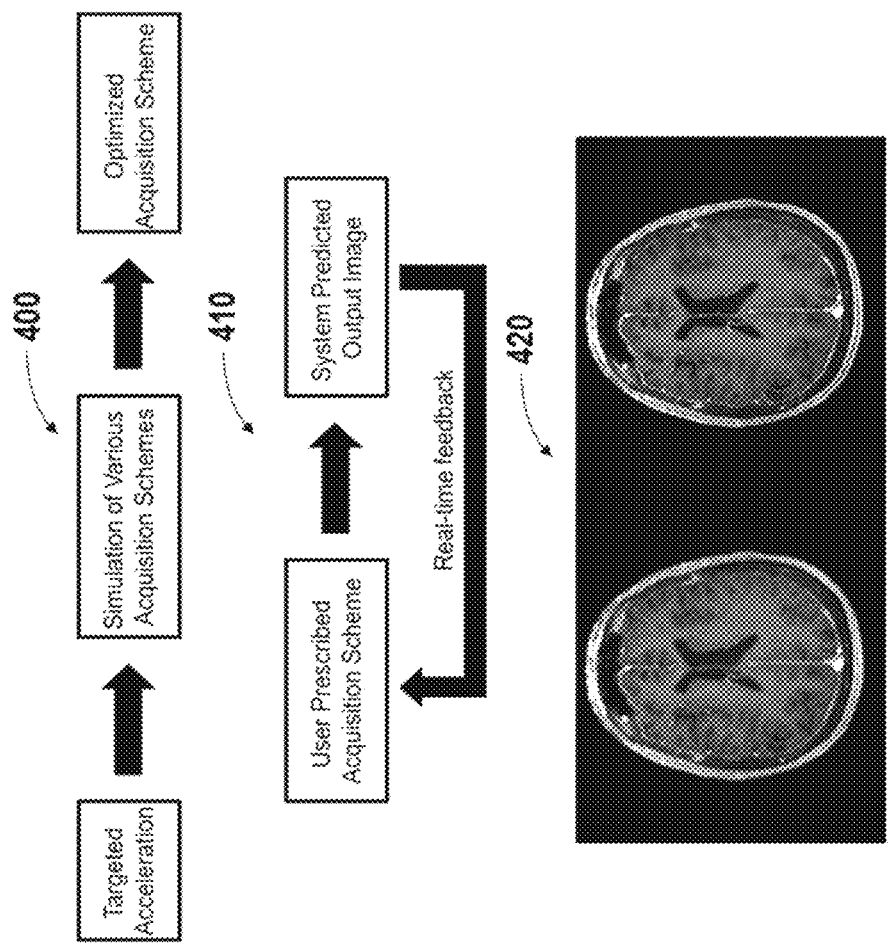
FIG. 4 shows examples of determining an acquisition scheme using an interactive MRI acquisition module.

FIG. 4 shows examples of determining an acquisition scheme via the aforementioned interactive MRI acquisition module. An acquisition scheme may be determined autonomously, semi-autonomously or manually. In a fully automated mode 400, the imaging accelerator may be configured to automatically determine an optimal acquisition scheme. For example, a user may input, via a user interface, a target acceleration. The target acceleration may be provided via any suitable formats on the aforementioned GUI, such as a selection from drop-down menu, manipulating a graphical element (e.g., slider bar), direct input in a text box (e.g., input an acceleration factor) or via other suitable means such as voice command and the like. The acceleration may be related to an aspect of image acquisition, including but not limited to, acceleration factor, acquisition speed, image resolution, field of view, and target region. In an example, the target acceleration may be a selection from 'fast acquisition', 'mid acquisition', 'slow acquisition.' In another example, the target acceleration may be an acceleration factor such as a factor of 1.5, 2, 3, 4, 5, 10, 15, 16, 17, 18, 19, 20, a factor of a value above 20 or below 1.5, or a value between any two of the aforementioned values.

In some embodiments, in response to receiving the target acceleration, a simulation of one or more acquisition schemes may be performed in order to determine an optimal acquisition scheme. In some cases, the one or more acquisition schemes may be applied to image patches to increase computation speed in the simulation. The optimal acquisition scheme may be determined based on a predetermined rule. For instance, the optimal acquisition scheme may be determined based on the quality of the output image (patch). For example, an acquisition scheme meeting the target acceleration goal while providing the best quality images may be selected. In some cases, the determined acquisition scheme may be displayed to a user for further approval or further adjustment. The approved or determined acquisition scheme may be transmitted to the controller of the MRI system for controlling the imaging operation of the imaging system consistent with the disclosure herein.

In some case, a user may be allowed to define an acquisition scheme in a semi-autonomous fashion 410. A user may specify one or more parameters of an acquisition scheme. In response to receiving the acquisition scheme, the interactive MRI acquisition module may run simulations and output images associated with the acquisition scheme. A user may or may not further adjust the acquisition scheme so as to change the quality or other characteristics of the output images. In some instances, a user may be provided with system advised adjustment. In some instances, a user may manually adjust one or more parameters upon viewing the simulated output images on a display. In the illustrated example 420, a user may be presented a lower quality image (left) and a simulated higher quality image (right) that can be achieved under the current acquisition scheme. In some cases, the simulated image may be dynamically updated while the user adjusting one or more parameters of the acquisition scheme. The determined acquisition scheme may then be transmitted to the controller of the MRI system for controlling the operations of the imaging system as described elsewhere herein.

The present disclosure provides computer systems that are programmed to implement methods of the disclosure. Referring back to FIG. 3, a computer system 300 is programmed or otherwise configured to manage and/or implement an MR imaging accelerator and its operations. The computer system 300 can regulate various aspects of FIGS. 1-2 of the present disclosure, such as, for example, the magnetic system, accelerator training module, the image reconstruction module, the interactive MRI acquisition module, the user interface module, and the methods illustrated in FIG. 4 and FIG. 5.

The computer system 300 may include a central processing unit (CPU, also "processor" and "computer processor" herein), a graphic processing unit (GPU), a general-purpose processing unit, which can be a single core or multi core processor, or a plurality of processors for parallel processing. The computer system 300 can also include memory or memory location (e.g., random-access memory, read-only memory, flash memory), electronic storage unit (e.g., hard disk), communication interface (e.g., network adapter) for communicating with one or more other systems, and peripheral devices 335, 220, such as cache, other memory, data storage and/or electronic display adapters. The memory, storage unit, interface and peripheral devices are in communication with the CPU through a communication bus (solid lines), such as a motherboard. The storage unit can be a data storage unit (or data repository) for storing data. The computer system 300 can be operatively coupled to a computer network ("network") 230 with the aid of the communication interface. The network 230 can be the Internet, an internet and/or extranet, or an intranet and/or extranet that is in communication with the Internet. The network 230 in some cases is a telecommunication and/or data network. The network 230 can include one or more computer servers, which can enable distributed computing, such as cloud computing. The network 230, in some cases with the aid of the computer system 300, can implement a peer-to-peer network, which may enable devices coupled to the computer system 300 to behave as a client or a server.

The CPU can execute a sequence of machine-readable instructions, which can be embodied in a program or software. The instructions may be stored in a memory location, such as the memory. The instructions can be directed to the CPU, which can subsequently program or otherwise configure the CPU to implement methods of the present disclosure. Examples of operations performed by the CPU can include fetch, decode, execute, and writeback.

The CPU can be part of a circuit, such as an integrated circuit. One or more other components of the system can be included in the circuit. In some cases, the circuit is an application specific integrated circuit (ASIC).

The storage unit can store files, such as drivers, libraries and saved programs. The storage unit can store user data, e.g., user preferences and user programs. The computer system 300 in some cases can include one or more additional data storage units that are external to the computer system, such as located on a remote server that is in communication with the computer system through an intranet or the Internet.

The computer system 300 can communicate with one or more remote computer systems through the network 230. For instance, the computer system 300 can communicate with a remote computer system of a user or a participating platform (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 300 via the network 230.

Methods as described herein can be implemented by way of machine (e.g., computer processor) executable code stored on an electronic storage location of the computer system 300, such as, for example, on the memory or electronic storage unit. The machine executable or machine readable code can be provided in the form of software. During use, the code can be executed by the processor. In some cases, the code can be retrieved from the storage unit and stored on the memory for ready access by the processor. In some situations, the electronic storage unit can be precluded, and machine-executable instructions are stored on memory.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 300, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 300 can include or be in communication with an electronic display 335 that comprises a user interface (UI) 340 for providing, for example, displaying reconstructed images, acquisition schemes, for example. Examples of UI's include, without limitation, a graphical user interface (GUI) and web-based user interface. The GUI can be rendered by the user interface module 308.

Methods and systems of the present disclosure can be implemented by way of one or more algorithms. An algorithm can be implemented by way of software upon execution by the central processing unit. For example, some embodiments use the algorithm illustrated in FIG. 4 and FIG. 5 or other algorithms provided in the associated descriptions above.

Figure 5:
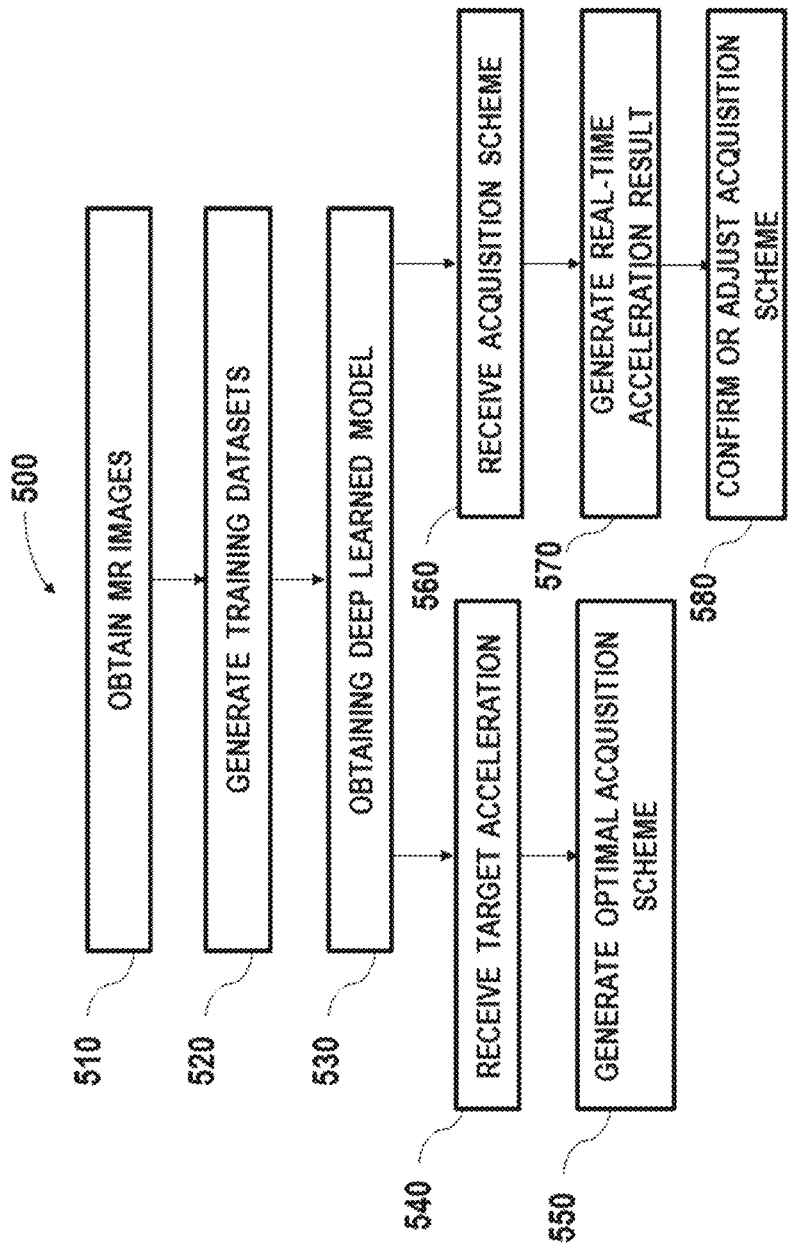
FIG. 5 illustrates an example of method for improving MR image quality with accelerated acquisition.

FIG. 5 illustrates an example of method 500 for improving MR image quality with accelerated acquisition. MR images may be obtained from MR imaging system (operation 510) for training a deep learning model. The MR images may be used to form training datasets (operation 520). The training dataset may comprise relatively lower quality image data and corresponding higher quality image data (i.e., ground truth data). The training dataset may comprise low quality images obtained from imaging devices. For example, the low quality input image can be simply obtained via inverse Fourier Transform (FT) of undersampled data (e.g., k-space data). The training dataset may comprise augmented datasets obtained from simulation. For instance, image data from clinical database may be used to generate low quality image data. In an example, FFT and filters may be applied to raw image data to transform it to low quality image data such as by applying masks to remove certain data points so as to create artifacts. Similarly, higher quality input image data may be obtained from direct image acquisition with longer acquisition time. In an example, training dataset may be 3D volume image data comprising multiple axial slices, and each slice may be complex-valued images each may include two channels for real and imaginary components.

The training step 530 may comprise a deep learning algorithm consistent with the disclosure herein. The deep learning algorithm may be a convolutional neural network, for example. In some cases, the deep learning algorithm may be a deep residual learning network. The trained accelerator may then be used for transforming a lower quality MR image into a higher quality MR image with a selected acceleration scheme. The acceleration scheme may be determined by receiving a target acceleration from a user (operation 540) then performing simulations on a plurality of acquisition schemes to determine an optimal acquisition scheme (operation 550). Alternatively or in addition to, the acquisition scheme may be determined by receiving a user specified acquisition scheme (operation 540) then generating real-time simulation results (operation 570) to show the simulated output images under the acquisition scheme (operation 570). A user may confirm or further adjust the acquisition scheme upon viewing the simulated output images (operation 580).

Although FIG. 5 shows a method in accordance with some embodiments a person of ordinary skill in the art will recognize that there are many adaptations for various embodiments. For example, the operations can be performed in any order. Some of the operations may be precluded, some of the operations may be performed concurrently in one step, some of the operations repeated, and some of the operations may comprise sub-steps of other operations.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein A and/or B encompasses one or more of A or B, and combinations thereof such as A and B. It will be understood that although the terms "first," "second," "third" etc. are used herein to describe various elements, components, regions and/or sections, these elements, components, regions and/or sections should not be limited by these terms. These terms are merely used to distinguish one element, component, region or section from another element, component, region or section. Thus, a first element, component, region or section discussed herein could be termed a second element, component, region or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Reference throughout this specification to "some embodiments," or "an embodiment," means that a particular feature, structure, or characteristic described in connection with the embodiment is included in at least one embodiment. Thus, the appearances of the phrase "in some embodiment," or "in an embodiment," in various places throughout this specification are not necessarily all referring to the same embodiment. Furthermore, the particular features, structures, or characteristics may be combined in any suitable manner in one or more embodiments.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A computer-implemented method for improving image quality with shortened acquisition time, the method comprising:
   (a) determining an accelerated image acquisition scheme for imaging a subject using a medical imaging apparatus, wherein the accelerated image acquisition scheme comprises one or more parameters related to at least one of an undersampled k-space, an undersampling pattern, and a reduced number of repetitions, and wherein the accelerated image acquisition scheme is determined based on user input and real-time simulated output images;
   (b) acquiring, using the medical imaging apparatus, a medical image of the subject according to the accelerated image acquisition scheme, wherein the medical image comprises a magnetic resonance image;
   (c) applying a deep network model to the medical image to improve the quality of the medical image; and
   (d) outputting an improved quality image of the subject for analysis by a physician.

2. The computer-implemented method of claim 1, wherein determining the accelerated image acquisition scheme comprises:
   (i) receiving a target acceleration factor or target acquisition speed via a graphical user interface, and
   (ii) selecting the accelerated image acquisition scheme from a plurality of accelerated image acquisition schemes based on the target acceleration factor or the target acquisition speed.

3. The computer-implemented method of claim 2, wherein selecting the accelerated image acquisition scheme comprises applying the plurality of accelerated image acquisition schemes to a portion of the medical image for simulation.

4. The computer-implemented method of claim 1, wherein the undersampling pattern, a random undersampling pattern is selected from a group consisting of a uniform undersampling pattern, a random undersampling pattern, and a variable undersampling pattern.

5. The computer-implemented method of claim 1, wherein the medical image comprises undersampled k-space image or image acquired using reduced number of repetitions.

6. The computer-implemented method of claim 1, wherein the deep learning model is trained with adaptively optimized metrics based on user input and real-time simulated output images.

7. The computer-implemented method of claim 1, wherein the deep learning model is trained using training datasets comprising at least a low quality image and a high quality image.

8. The computer-implemented method of claim 7, wherein the low quality image is generated by applying one or more filters or adding synthetic noise to the high quality image to create noise or undersampling artifacts.

9. The computer-implemented method of claim 1, wherein the deep learning model is trained using image patches that comprise a portion of at least a low quality image and a high quality image.

10. The computer-implemented method of claim 9, wherein the image patches are selected based on one or more metrics quantifying an image similarity.

11. The computer-implemented method of claim 1, wherein the deep learning model is a deep residual learning model.

12. The computer-implemented method of claim 1, wherein the deep learning model is trained by adaptively tuning one or more model parameters to approximate a reference image.

13. The computer-implemented method of claim 1, wherein the improved quality image of the subject has greater signal-to-noise ratio (SNR), higher resolution, or less aliasing compared with the medical image acquired using the medical imaging apparatus.

14. A non-transitory computer-readable storage medium including instructions that, when executed by one or more processors, cause the one or more processors to perform operations comprising:
   (a) determining an accelerated image acquisition scheme for imaging a subject using a medical imaging apparatus, wherein the accelerated image acquisition scheme comprises one or more parameters related to at least one of an undersampled k-space, an undersampling pattern, and a reduced number of repetitions, and wherein the accelerated image acquisition scheme is determined based on user input and real-time simulated output images;
   (b) acquiring, using the medical imaging apparatus, a medical image of the subject according to the accelerated image acquisition scheme, wherein the medical image comprises a magnetic resonance image;
   (c) applying a deep network model to the medical image to improve the quality of the medical image; and
   (d) outputting an improved quality image of the subject for analysis by a physician.

* * * * *